US009433592B2

(12) United States Patent
Rosa-Calatrava et al.

(10) Patent No.: US 9,433,592 B2
(45) Date of Patent: Sep. 6, 2016

(54) PHARMACEUTICAL OR VETERINARY ANTIVIRAL COMPOSITIONS

(75) Inventors: Manuel Rosa-Calatrava, Lyons (FR); Jean-Jacques Diaz, Venissieux (FR); Julien Textoris, Marseilles (FR); Laurence Josset, Lyons (FR)

(73) Assignees: UNIVERSITE CLAUDE BERNARD LYON 1 (FR); CENTRE NATIONAL DE LA RECHERCHE SCIENTIFIQUE (CNRS) (FR); HOSPICES CIVILS DE LYON (FR)

( * ) Notice: Subject to any disclaimer, the term of this patent is extended or adjusted under 35 U.S.C. 154(b) by 370 days.

(21) Appl. No.: 13/513,877

(22) PCT Filed: Dec. 7, 2010

(86) PCT No.: PCT/EP2010/069023

§ 371 (c)(1), (2), (4) Date: Sep. 11, 2012

(87) PCT Pub. No.: WO2011/069990

PCT Pub. Date: Jun. 16, 2011

(65) Prior Publication Data

US 2013/0012502 A1 Jan. 10, 2013

Related U.S. Application Data

(60) Provisional application No. 61/267,997, filed on Dec. 9, 2009.

(30) Foreign Application Priority Data

Dec. 9, 2009 (FR) ..................................... 09 58810

(51) Int. Cl.

| | |
|---|---|
| ***A61K 31/16*** | (2006.01) |
| ***A61K 31/215*** | (2006.01) |
| ***A61K 31/165*** | (2006.01) |
| ***A61K 31/13*** | (2006.01) |
| ***A61K 31/135*** | (2006.01) |
| ***A61K 31/137*** | (2006.01) |
| ***A61K 31/195*** | (2006.01) |
| ***A61K 31/221*** | (2006.01) |
| ***A61K 31/351*** | (2006.01) |
| ***A61K 31/404*** | (2006.01) |
| ***A61K 31/421*** | (2006.01) |
| ***A61K 31/437*** | (2006.01) |
| ***A61K 31/542*** | (2006.01) |
| ***A61K 45/06*** | (2006.01) |

(52) U.S. Cl.

CPC ............ *A61K 31/165* (2013.01); *A61K 31/13* (2013.01); *A61K 31/135* (2013.01); *A61K 31/137* (2013.01); *A61K 31/195* (2013.01); *A61K 31/215* (2013.01); *A61K 31/221* (2013.01); *A61K 31/351* (2013.01); *A61K 31/404* (2013.01); *A61K 31/421* (2013.01); *A61K 31/437* (2013.01); *A61K 31/542* (2013.01); *A61K 45/06* (2013.01)

(58) Field of Classification Search

CPC .......................... A61K 31/165; A61K 31/215
USPC ...................... 514/626, 649, 226.5, 377, 529
See application file for complete search history.

(56) References Cited

U.S. PATENT DOCUMENTS

2007/0010578 A1* 1/2007 Chien et al. ................. 514/483

FOREIGN PATENT DOCUMENTS

| | | |
|---|---|---|
| WO | 2007044752 A2 | 4/2007 |
| WO | 2008099175 A1 | 8/2008 |
| WO | 2009047298 A2 | 4/2009 |
| WO | 2009065116 A1 | 5/2009 |

OTHER PUBLICATIONS

French Preliminary Search Report issued from corresponding FR0958810, dated Apr. 27, 2010.
International Search Report issued from corresponding PCT/EP2010/069023, dated Apr. 7, 2011.
Gebhardt, et al., "Propranolol Suppresses Reactivation of Herpesvirus", Antiviral Research, Jan. 17, 1995, pp. 255-261, vol. 27, Elsevier B.V., NL.
Hayden, Frederick, "Developing New Antiviral Agents for Influenza Treatment: What Does the Future Hold?", Clinical Infectious Diseases, Jan. 1, 2009, pp. S2-S12, vol. 48, Chicago IL, US.
Josset, et al., "Gene Expression Signature-Based Screening Identifies New Broadly Effective Influenza A Antivirals", Plos One, Oct. 4, 2010, pp. 1-18, vol. 5, US.
McClellan, et al., "Midodrine a Review of its Therapeutic Use in the Management of Orthostatic Hypotension", Drugs & Aging, Jan. 1, 1998, pp. 75-86, vol. 12, Auckland, NZ.
Reid, John, "Update on Rilmenidine: Clinical Benefits", American Journal of Hypertension, Jan. 1, 2001, pp. 322S-324S, vol. 14, New York, NY, US.
Schmidtke, et al., "Do Oxymetazoline-Containing Nasal Sprays Exhibit an Antiviral Activity Against Influenza A Virus?", Chemotherapie Journal, Dec. 6, 2005, pp. 207-211, vol. 14, DE.
Supuran, Claudiu, "Carbonic Anhydrases, Novel Therapeutic Applications for Inhibitors and Activators", Nature Reviews Drug Discovery, Feb. 2, 2008, pp. 168-181, vol. 7, GB.

* cited by examiner

*Primary Examiner* — Shengjun Wang
(74) *Attorney, Agent, or Firm* — Banner & Witcoff, Ltd.

(57) ABSTRACT

Pharmaceutical or veterinary compositions to prevent or treat viral infections, in particular to prevent or treat influenza A, B and C virus infections.

4 Claims, 18 Drawing Sheets

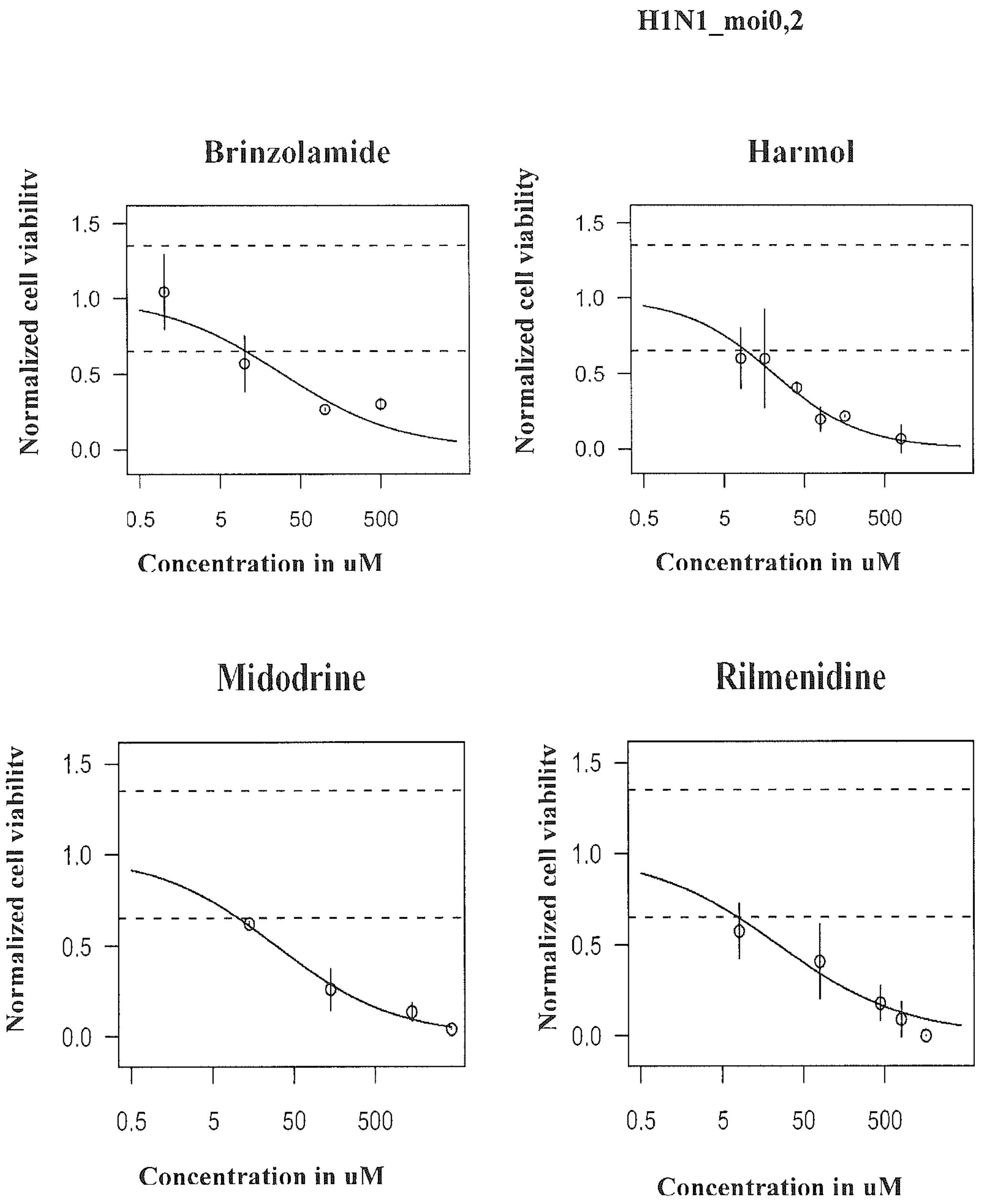
FIG. 2.A

H1N1sw1_moi2
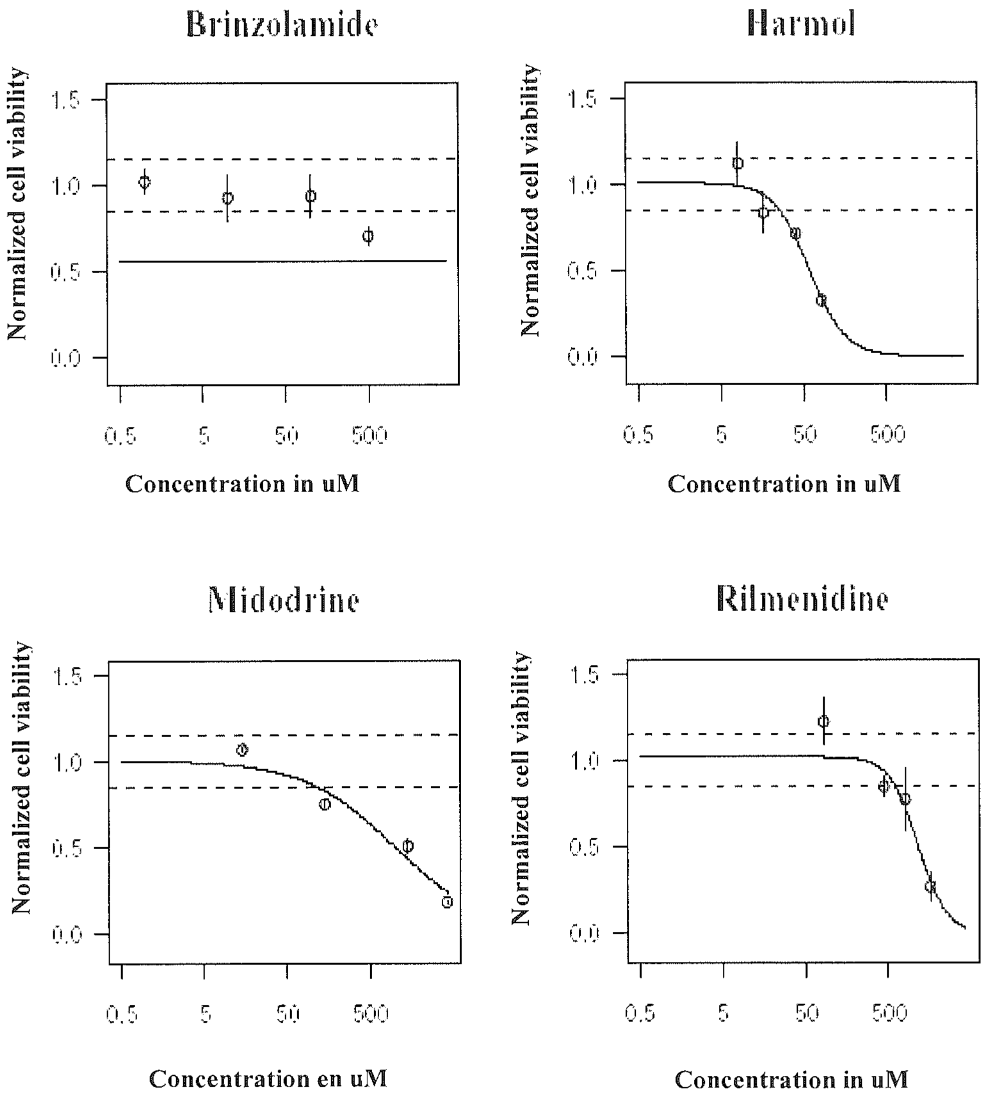
FIG. 2.B

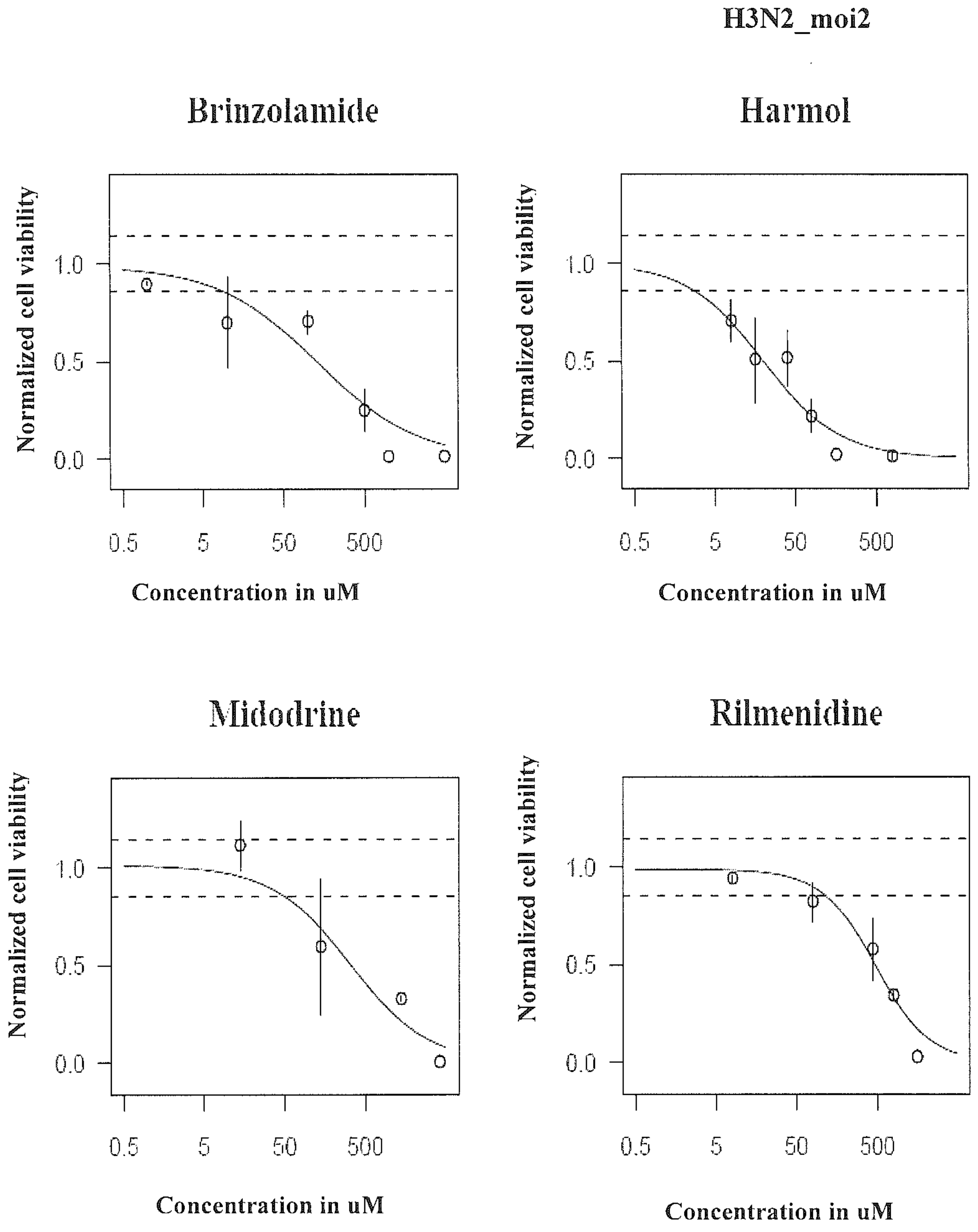
FIG. 2.C

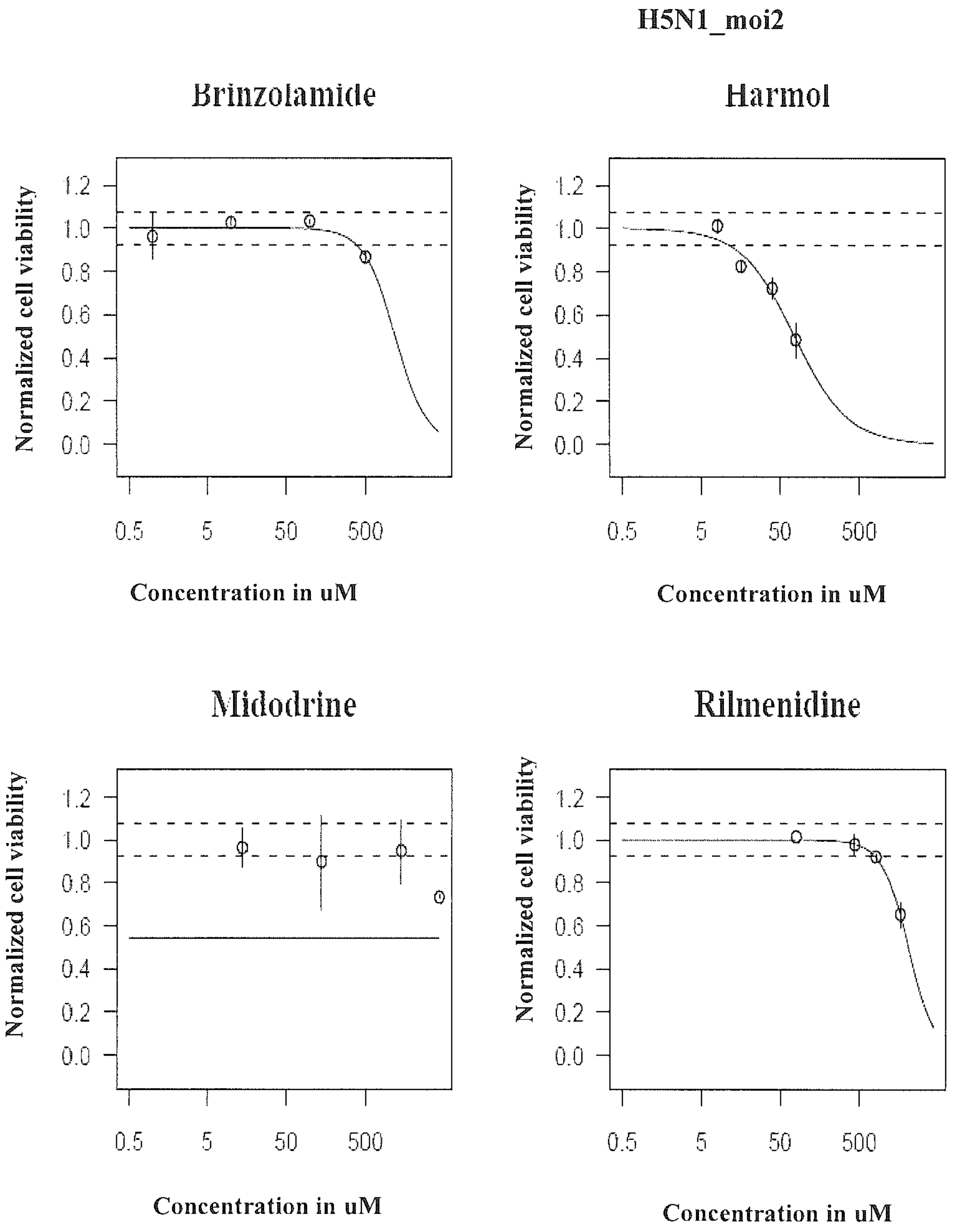
FIG. 2.D

H5N2_moi0,2
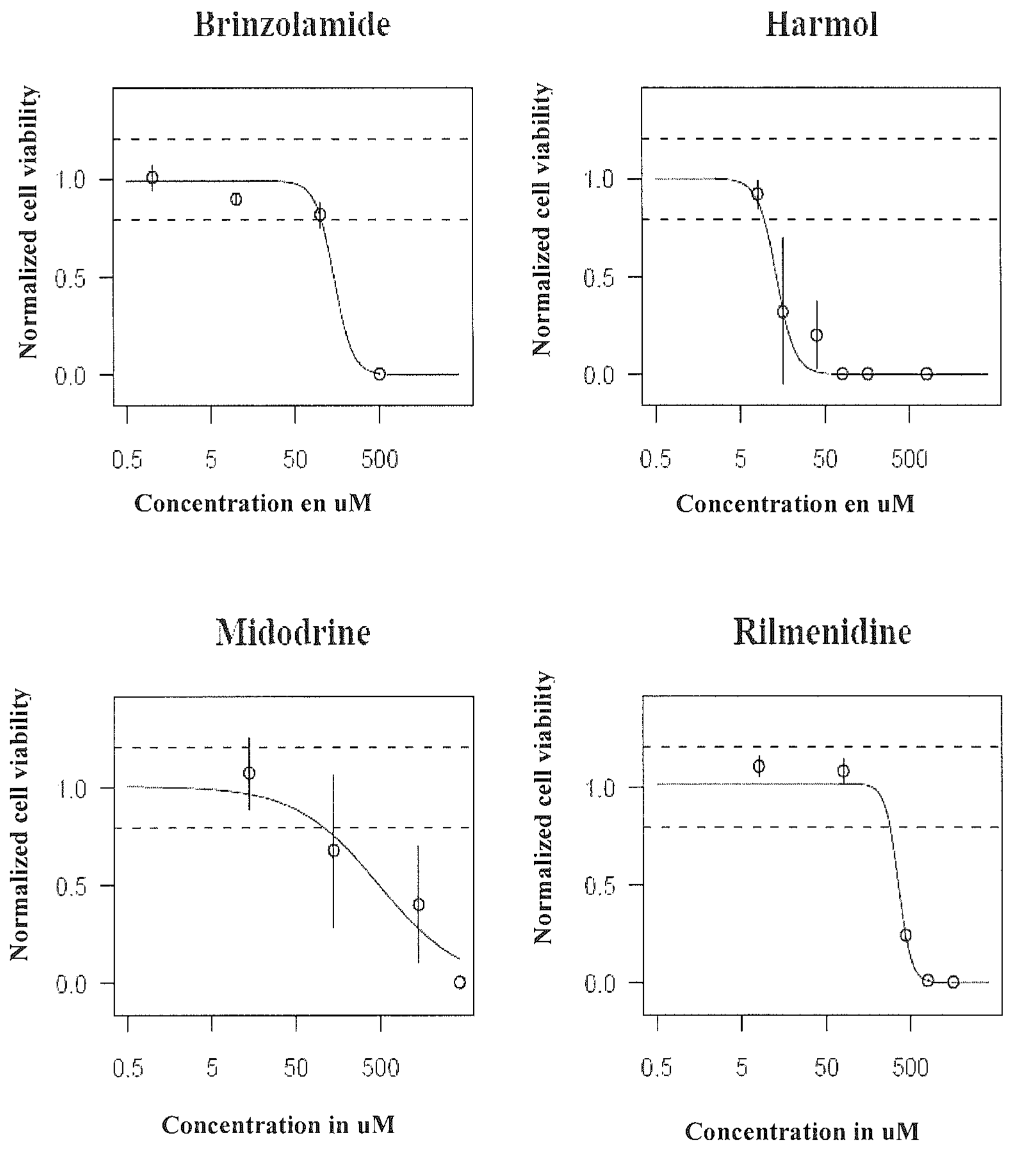
FIG. 2.E

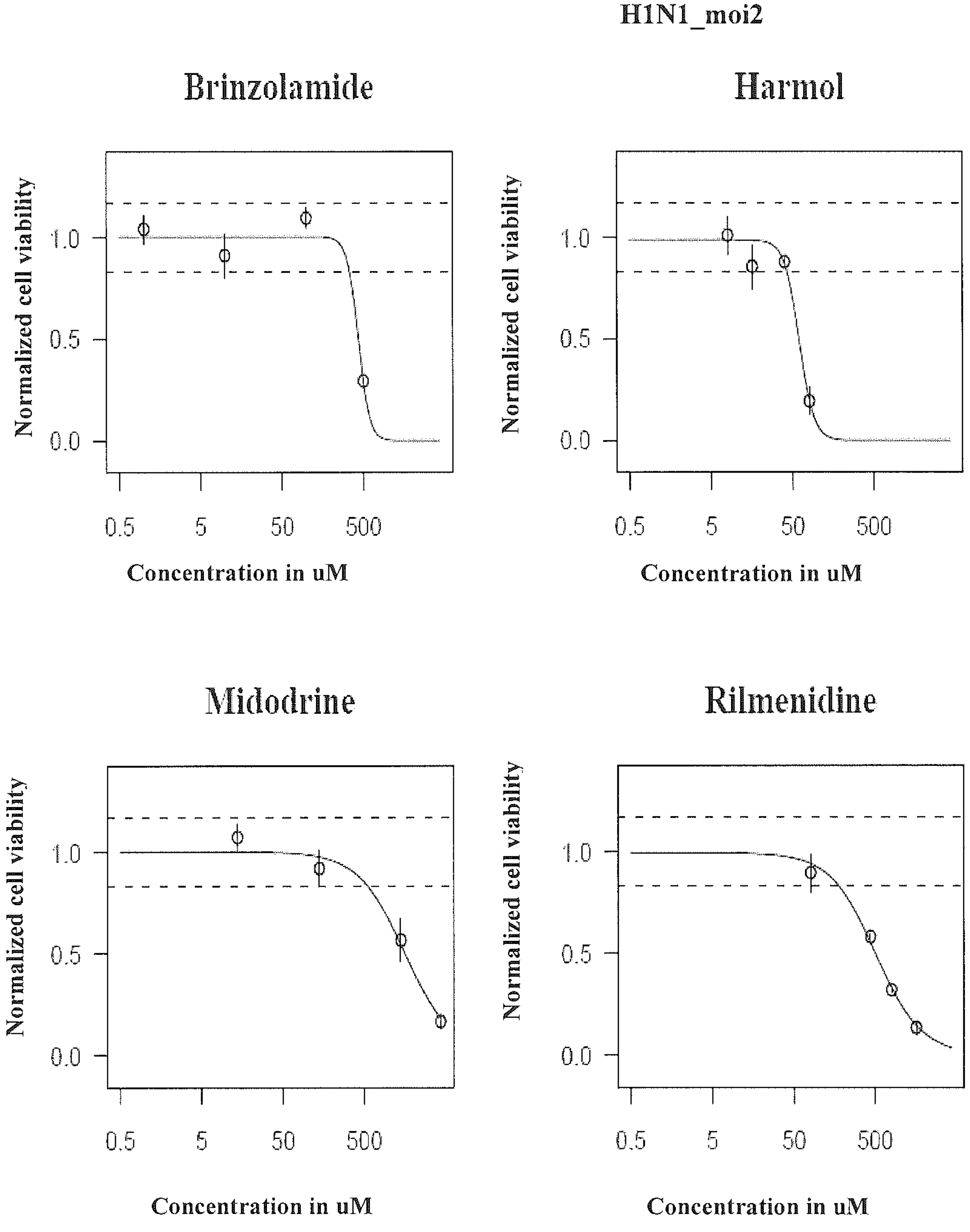
FIG. 2.F

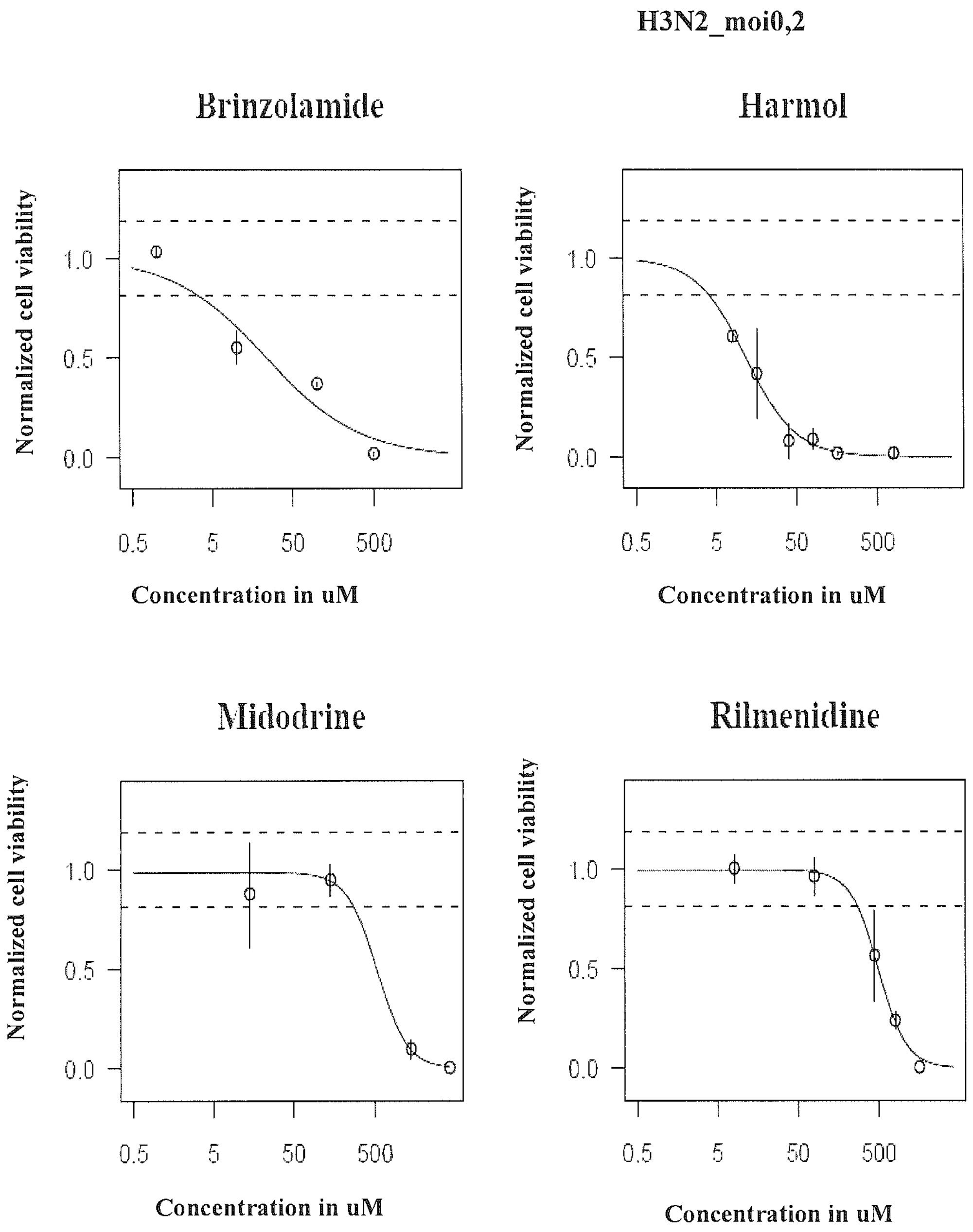
FIG. 2.G

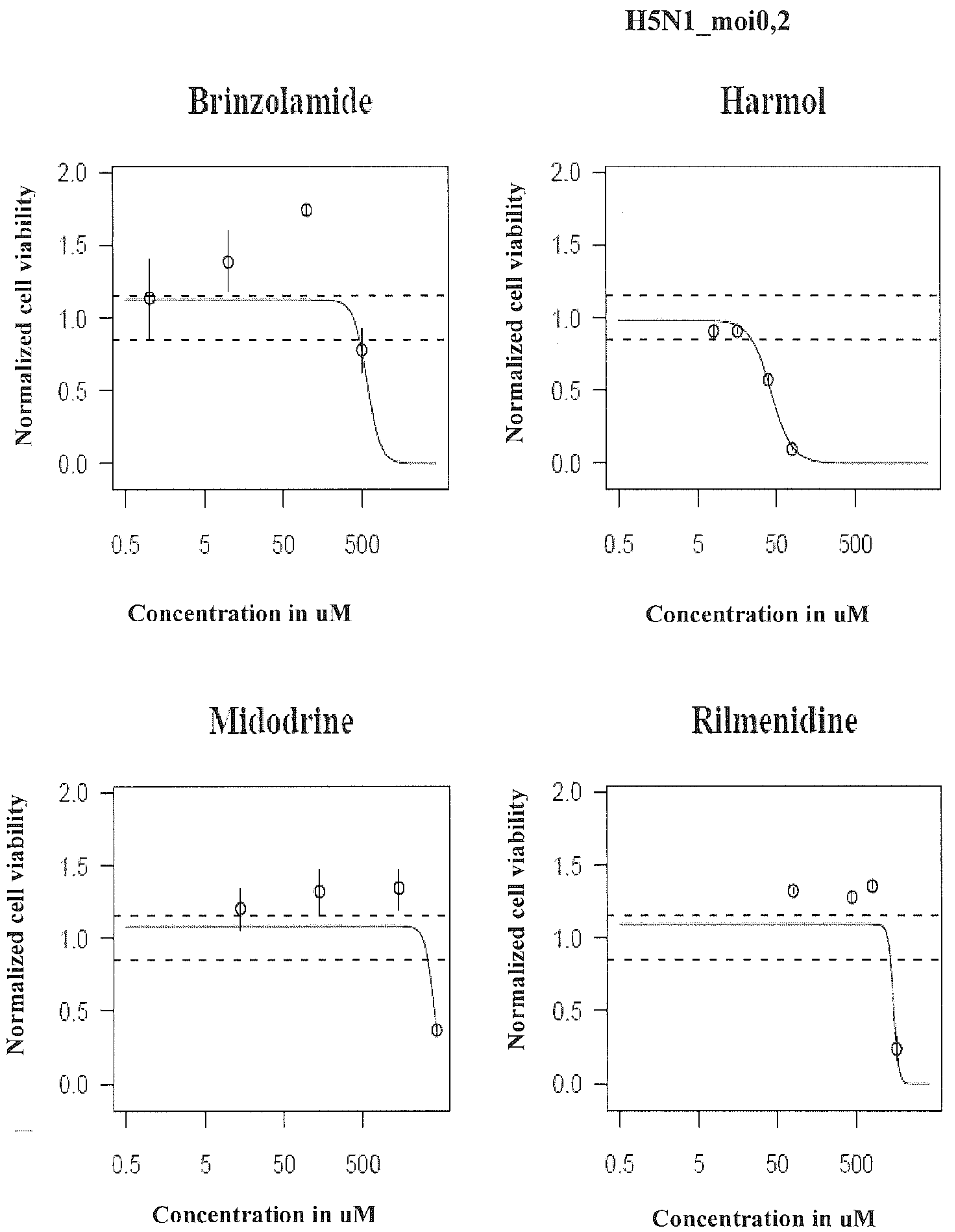
FIG. 2.H

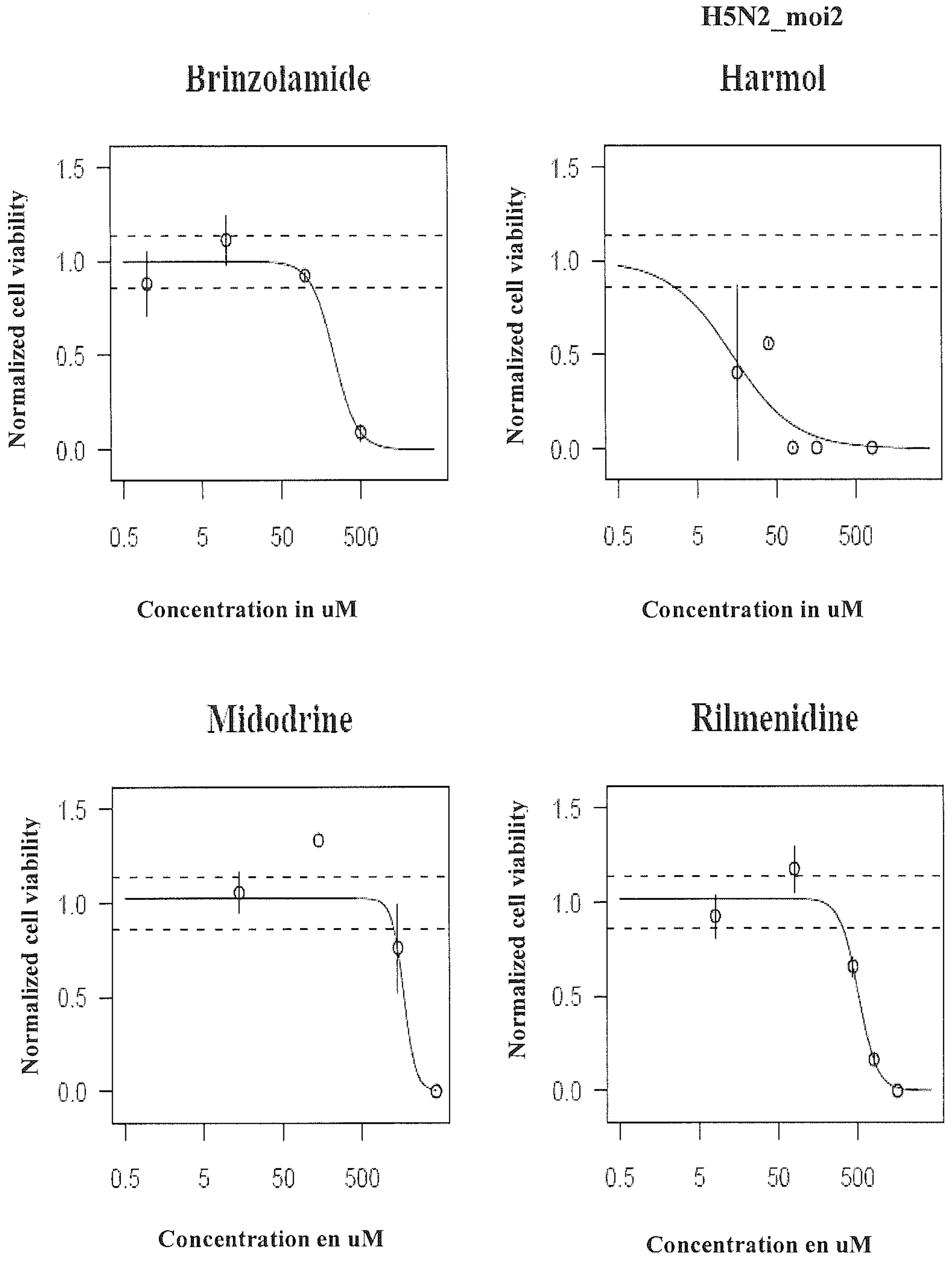
FIG. 2.I

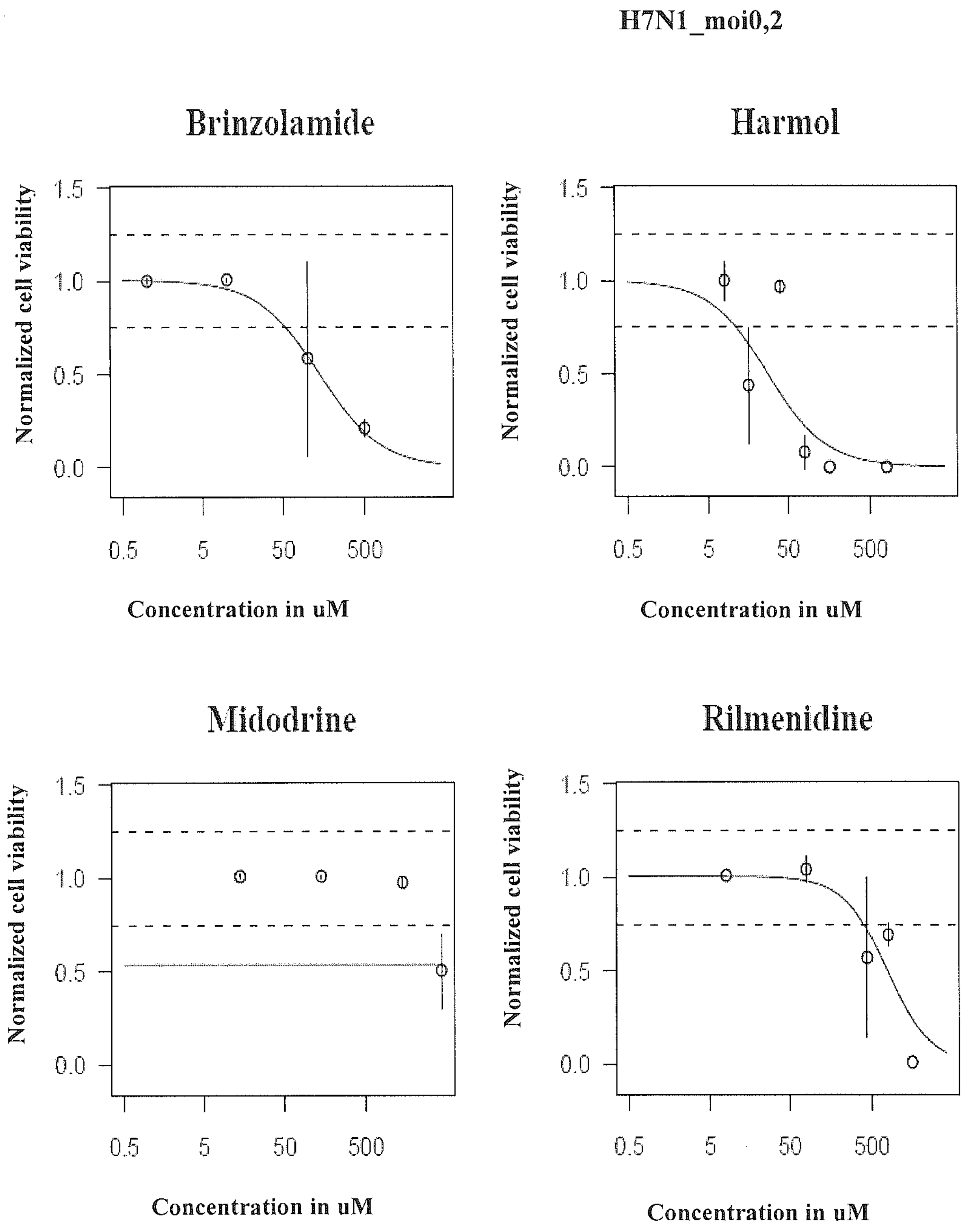
FIG. 2.J

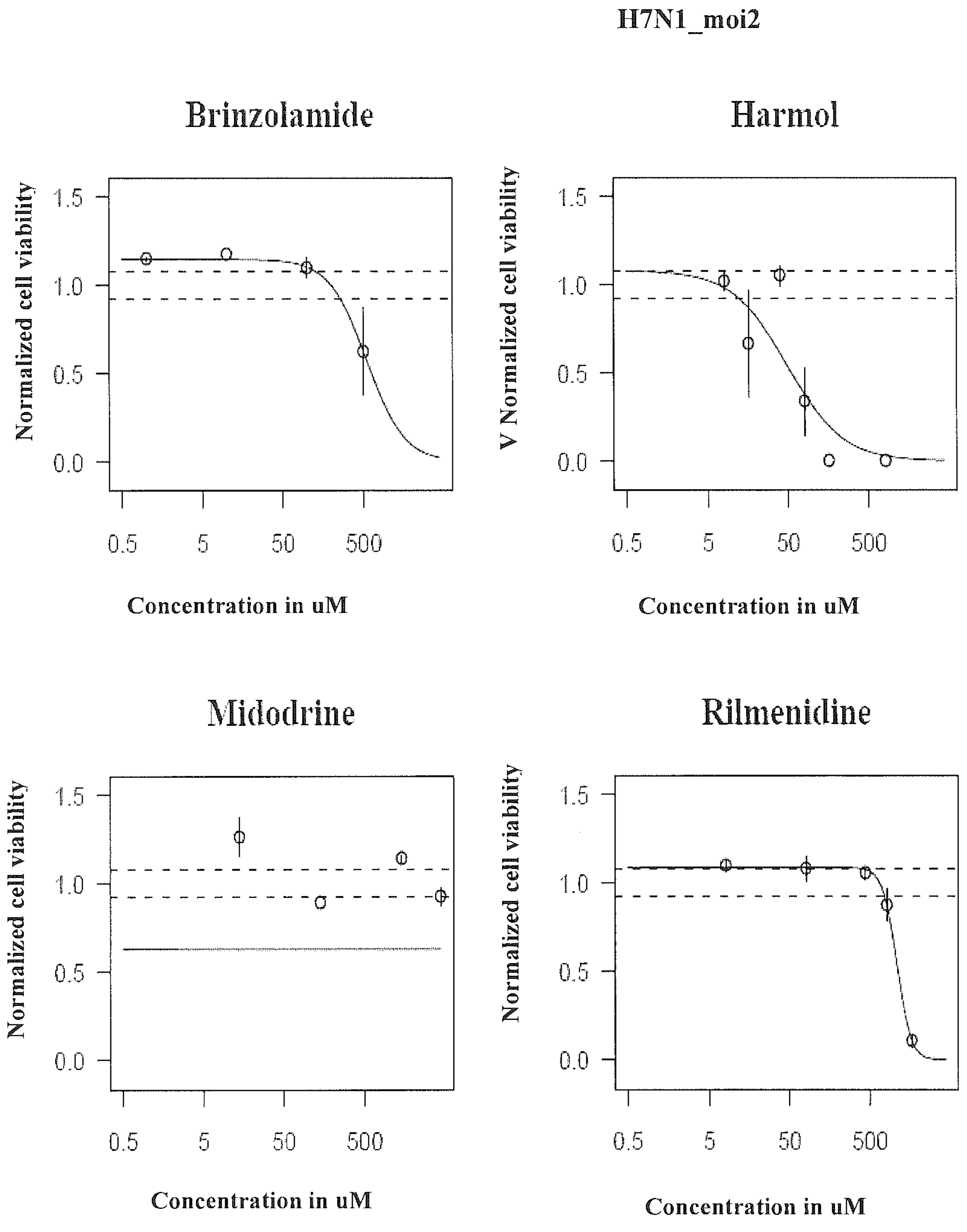
FIG. 2.K

| | | H1N1 moi 2 | | H1N1 moi 0.2 | |
|---|---|---|---|---|---|
| molecules | CC50 (uM) | EC50 (uM) | SI = CC50/EC50 | EC50 (uM) | SI = CC50/EC50 |
| Midodrine | > 4250 | 1566,70 | > 2,71 | 29,816741 | > 142,52 |
| Harmol | 94,98 | 60,361696 | 1,57 | 20,530557 | 4,63 |
| Brinzolamide | 665,51 | 435,064415 | 1,53 | 28,952263 | 22,99 |
| Rilmenidine | 1125,3 (1550,7)* | 506,22 (>1600)** | 2,22 (ND) | 24,22 (173,63)*** | 46,46 (8,93) |
| | * p = 0,0026 | ** p = ND | | ***p = 7e-04 | |

FIG. 4.A

| | | H5N1 moi 2 | | H5N1 moi 0,2 | |
|---|---|---|---|---|---|
| molecules | CC50 (uM) | EC50 (uM) | SI = CC50/EC50 | EC50 (uM) | SI = CC50/EC50 |
| Midodrine | > 4250 | > 4250 | ND | 3896,30 | > 1,09 |
| Harmol | 94,98 | 77,49321 | 1,23 | 43,364315 | 2,19 |
| Brinzolamide | 665,51 | > 500 | ND | > 500 | ND |
| Rilmenidine | 1125,3 (1550,7) * | 2037,7 (> 1600)** | 0,55 (ND) | 1466,8 (1829,6)*** | 0,77 (0,85) |
| | * p = 0,0026 | ** p = ND | | *** p = 0.40 | |

FIG. 4.B

| | | H5N2 moi 2 | | H5N2 moi 0,2 | |
|---|---|---|---|---|---|
| molecules | CC50 (uM) | EC50 (uM) | SI = CC50/EC50 | EC50 (uM) | SI = CC50/EC50 |
| Midodrine | > 4250 | 1,67E+003 | > 2.54 | 475,577774 | > 8,94 |
| Harmol | 94,98 | 4,061179 | 23,39 | 13,451719 | 7,06 |
| Brinzolamide | 665,51 | 232,395696 | 2,86 | 145,607914 | 4,57 |
| Rilmenidine | 1125,3 (1550,7) * | 514,32 (733,6)** | 2,19 (2,11) | 358,69 (564,1)*** | 3,14 (2,75) |
| | * p = 0,0026 | ** p = 2e-04 | | *** p = 0.1881 | |

FIG. 4.C

| | | H7N1 moi 2 | | H7N1 moi 0,2 | |
|---|---|---|---|---|---|
| molecules | CC50 (uM) | EC50 (uM) | SI = CC50/EC50 | EC50 (uM) | SI = CC50/EC50 |
| Midodrine | > 4250 | > 4250 | ND | > 4250 | ND |
| Harmol | 94,98 | 49,35 | 1,92 | 27,96 | 3,40 |
| Brinzolamide | 665,51 | 551,05 | 1,21 | 139,19 | 4,78 |
| Rilmenidine | 1125,3 (1550,7) * | 1050,4 (1109,3) | 1,07 (1,4) | 777,85 (801,08) | 1,45 (1,94) |
| | * p = 0,0026 | ** p = 0,53 | | *** p = 0,9 | |

FIG. 4.D

| | | H1N1 moi 2 | H1N1 moi 2 |
|---|---|---|---|
| molecules | CC50 (uM) | EC50 (uM) | SI |
| Midodrine | > 4250 | 987,243995 | > 4,3 |
| Harmol | 94,97532 | 57,385447 | 1,655041913 |
| Brinzolamide | 665,51 | > 500 | < 1,33 |
| Rilmenidine | 1125,3 (1550,7) * | 1125,8 (923,38)** | 1 (1,68) |
| | * p = 0,0026 | ** p = 0,53 | |

FIG. 4.E

PHARMACEUTICAL OR VETERINARY ANTIVIRAL COMPOSITIONS

RELATED APPLICATION DATA

This application is a National Stage application under 35 U.S.C. 371 of PCT application PCT/EP2010/069023 designating the United States and filed Dec. 7, 2010; which claims the benefit of FR patent application number 0958810 and filed Dec. 9, 2009 and U.S. provisional application No. 61/267,997 and filed Dec. 9, 2009, each of which are hereby incorporated by reference in their entireties.

The invention relates to compositions used to treat viral infections and in particular to treat pathologies related to influenza virus infection in man and animals.

The molecules responsible for the flu are the influenza viruses, which are divided into three types: A, B and C. Located on the surface of the viruses are two glycoproteins which play an important role in the infection of cells of the infected organism: hemagglutinin (HA) and neuraminidase (NA). There are various influenza A virus subtypes according to the nature of the HA and NA glycoproteins on their surface: 16 types of HA and nine types of NA have been identified in viruses circulating among migratory sea birds. In man, with viruses circulating for several decades, subtypes H1N1, H2N2 and H3N2 are found, with occasional interspecies transmission (from animal to man) of avian viruses H5N1, H7N7, H5N2 and H9N2. Influenza viruses can thus be defined by the type of protein on their surface.

As the recent emergence of a new pandemic H1N1 influenza virus of porcine, avian and human origin demonstrates (porcine, avian and human reassortant virus), influenza A viruses are a serious threat to public health. Flu pandemics are the result of antigenic shifts corresponding to the appearance of viruses bearing new surface glycoproteins (HA and NA) in the human population. These shifts can be due to the direct transmission in man of avian viruses (the case of epidemics of highly pathogenic avian H5N1 since 2003 in Asia or of the H7N7 influenza epidemic in the Netherlands in 2003). Antigenic shifts can also be due to a genetic rearrangement between avian, porcine and human viruses, with pigs playing the role of intermediate host. This genetic readaptation is the source of the current H1N1 pandemic. Furthermore, seasonal flu epidemics are a major cause of increased morbidity and mortality, especially in the very young, the old, the immunosuppressed and those with cardiopulmonary disease.

Vaccination remains the cornerstone of flu prevention. However, when a new virus appears, time is needed for its development (six to nine months) and the use of antiviral drugs must be considered for treatment or prevention. Current antivirals are M2 channel inhibitors (amantadine) and neuraminidase inhibitors (zanamivir and oseltamivir). The use of these drugs can be limited by the rapid appearance of resistance, which has already appeared for the pandemic H1N1 virus (genetic drift by accumulation of mutations). Moreover, it cannot be excluded that new emerging viruses are also resistant to these molecules. Finally, most of these molecules cannot be administered systemically, which poses a problem in the event of serious infections. It thus appears necessary to develop new antivirals that have a broad spectrum of action and that are easier to administer.

International application WO 2007/044752 relates to compositions to treat skin disorders. These compositions comprise an alpha-adrenergic receptor antagonist such as midodrine. This document comprises no disclosure or teaching as to the use of products comprising midodrine or desglymidodrine to treat viral infections.

International application WO 2009/065116 relates to methods for treating purpura with compositions comprising midodrine and another active agent, which can be an antiviral. This document does not describe the use of products comprising midodrine or desglymidodrine to treat viral infections.

A solution for the development of new broad spectrum therapies is to aim at the cellular factors essential to viral replication. This strategy was notably developed with relative success against retroviruses. In the context of the present invention, several molecules were selected and evaluated in a cellular test of viral infection. Certain molecules had an antiviral effect not only on a set of reference influenza viruses (H1N1, H3N2, H5N2, H7N7 and H5N1), but also on the pandemic H1N1 virus (A/California/07/2009) and related field strains.

The selected compounds had been described as active ingredients in the treatment of pathologies quite removed from viral infections. Unexpectedly, it has now been shown that these compounds have antiviral activity and in particular anti-influenza activity against various influenza virus subtypes.

SUMMARY OF THE INVENTION

The invention relates to pharmaceutical or veterinary compositions for use to prevent or treat viral infections, comprising at least one compound selected from midodrine, desglymidodrine, harmol, harmol dimers, brinzolamide, rilmenidine and derivatives thereof.

In a first embodiment, at least one compound is selected from midodrine, desglymidodrine and derivatives thereof.

In a second embodiment, at least one compound is selected from harmol, harmol dimers and derivatives thereof.

In a third embodiment, at least one compound is selected from brinzolamide and derivatives thereof.

In a fourth embodiment, at least one compound is selected from rilmenidine and derivatives thereof.

In a preferred embodiment, the pharmaceutical or veterinary compositions of the invention are for use to prevent or treat influenza virus infections (influenza virus A, B and C).

Preferentially, the pharmaceutical or veterinary compositions of the invention further comprise a suitable pharmaceutical carrier.

Preferentially, the pharmaceutical or veterinary compositions of the invention further comprise another antiviral or anti-influenza agent.

Preferably, the antiviral or anti-influenza agent is selected from oseltamivir, zanamivir, peramivir, amantadine, rimantadine, ribavirin and arbidol.

The invention further relates to a product comprising a compound selected from midodrine, desglymidodrine, harmol, harmol dimers, brinzolamide and rilmenidine, as well as another antiviral agent as a combination product for simultaneous, separated or staggered use in therapy, and in particular in the prevention and treatment of viral infections.

The invention further relates to the use of at least one compound selected from midodrine, desglymidodrine, harmol, harmol dimers, brinzolamide and rilmenidine and derivatives thereof for the manufacture of a drug to prevent or treat influenza.

DESCRIPTION OF THE INVENTION

The present invention relates to pharmaceutical or veterinary compositions for the prevention and treatment of viral infections in man and in animals and more particularly for the treatment of influenza. These compositions comprise at least one compound selected from midodrine, desglymidodrine, harmol, harmol dimers, brinzolamide and rilmenidine and derivatives thereof. These compounds are known for use in other therapeutic applications with no relation to antiviral activity in man or animals. It is now demonstrated that these compounds, unexpectedly, have antiviral activity and in particular anti-influenza activity against various subtypes of influenza virus A and influenzas B and C.

Midodrine has been described for the treatment of orthostatic hypotension. It is a prodrug that after hydrolysis yields desglymidodrine, which is the active metabolite of midodrine.

Various pharmaceutically acceptable salts of midodrine or of desglymidodrine can be used in the compositions of the present invention, and preferably the midodrine is in the form of midodrine hydrochloride represented below:

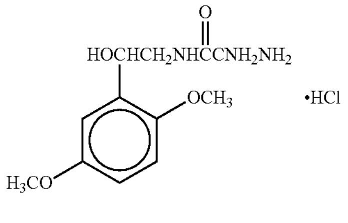

Acetamide, 2-amino-N-[2-(2,5-dimethoxyphenyl)-2-hydroxyethyl]-monohydrochloride, (±)-; (2)(±)-2-amino-N-(β-hydroxy-2,5-dimethoxyphenethyl)acetamide monohydrochloride For the antiviral treatment of an adult, the amount of midodrine administered is preferably between 1 mg and 30 mg per day, more preferentially between 7.5 mg and 15 mg per day.

Harmol is one of the alkaloids extracted from *Peganum harmala* and this compound has been described for antitumor activity.

Harmol is represented below:

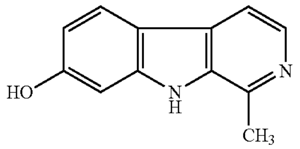

1-Methyl-9H-beta-carbolin-7-ol

Various pharmaceutically acceptable harmol salts can be used in the compositions of the present invention, and preferably the harmol is in the form of harmol hydrochloride.

The compositions with antiviral activity and, more particularly, anti-influenza activity of the present invention can further comprise a harmol dimer. Harmol dimers are notably described in international application WO 2009/047298: these harmol dimers have reduced cytotoxicity.

Harmol dimers are preferably of the following general formula:

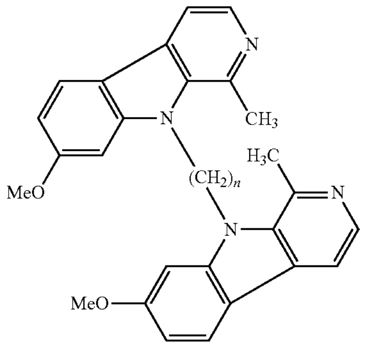

wherein N is an integer between 2 and 10 and preferably between 3 and 5.

In a preferred embodiment of the present invention, the harmol dimer has the following formula:

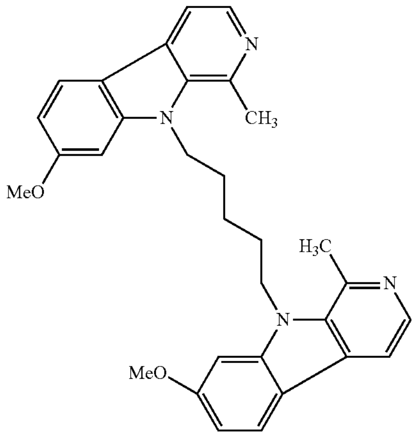 [SMILES: COc1ccc2c3ccnc(C)c3n(CCCCCn3c4cc(OC)ccc4c4ccnc(C)c43)c2c1]

For the antiviral treatment of an adult, the dose of harmol or of harmol dimer administered is typically between 0.5 mg and 100 mg per day, more preferentially the dose administered is between 1 mg and 50 mg per day.

Brinzolamide is a carbonic anhydrase inhibitor used by ocular route in the treatment of intraocular hypertension and open-angle glaucoma.

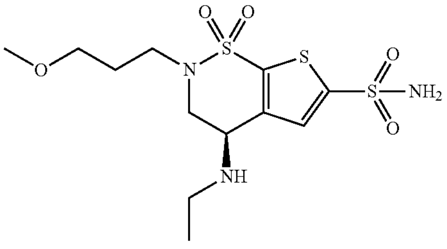 [SMILES: CCN[C@H]1CN(CCCOC)S(=O)(=O)c2sc(S(N)(=O)=O)cc21]

(R)-(+)-4-Ethylamino-2-(3-methoxypropyl)-3,4-dihydro-2H-thieno[3,2-e]-1,2-thiazine-6-sulfonamide-1,1-dioxide For the antiviral treatment of an adult, the dose of brinzolamide administered is typically between 0.5 mg and 100 mg per day, more preferentially the dose administered is between 1 mg and 50 mg per day.

Rilmenidine has been described as an antihypertensive drug. Its chemical formula is

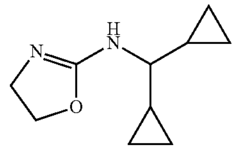 [SMILES: C1COC(NC(C2CC2)C2CC2)=N1]

Various pharmaceutically acceptable rilmenidine salts can be used in the compositions of the present invention, and preferably the rilmenidine is in the form of rilmenidine dihydrogen phosphate.

For the antiviral treatment of an adult, the dose of rilmenidine administered is between 1 mg and 50 mg per day, preferably between 1 mg and 10 mg per day and more preferentially the dose administered is 4 mg per day.

The pharmaceutical or veterinary compositions of the invention have antiviral activity and are suitable to prevent or treat various viral infections. In particular, the pharmaceutical or veterinary compositions are used to prevent or treat influenza virus infections (influenza A, B and C).

Advantageously, the compositions of the present invention have broad-spectrum activity against various types of influenza viruses (types A, B and C).

In another embodiment, the compositions of the present invention are to prevent and treat type A and type B virus infections.

In another embodiment, the compositions of the present invention are to prevent and treat type A virus infections circulating primarily in man and in animals.

In another embodiment, the compositions of the present invention are to prevent and treat type B virus infections circulating in man.

In another embodiment, the compositions of the present invention are to prevent and treat infections by type C viruses circulating in man and in pigs.

The invention thus relates to the prevention and treatment of influenza virus infections in man.

The invention further relates to the prevention and treatment of influenza virus infections in animals, in particular in domesticated animals such as pigs, horses and poultry. More particularly, the invention relates to the prevention and treatment of influenza virus infections in poultry and more particularly in hens, ducks, geese and turkeys. The invention further relates to the prevention and treatment of influenza virus infections in other animals such as, for example, cats, dogs and felids.

The present invention further relates to the prevention and treatment of other viral infections.

Preferably, the pharmaceutical or veterinary compositions of the invention comprise an active compound in a suitable pharmaceutical carrier.

These compositions can be formulated for administration to mammals, including man. Dosing varies according to the treatment and to the affection concerned. These compositions are typically prepared in such a way as to be able to be administered by the digestive or parenteral route.

In the pharmaceutical compositions of the present invention for oral, sublingual, subcutaneous, intramuscular, intravenous, transdermal, ocular, local or rectal administration, the active compound can be administered in unit dose forms of administration, in mixture with traditional pharmaceutical supports, in animals or in humans. Suitable unit dose forms of administration comprise oral forms such as tablets, gelatin capsules, powders, granules and oral solutions or suspensions, sublingual and buccal forms of administration, subcutaneous, intramuscular, intravenous, intranasal or intraocular forms of administration and rectal forms of administration.

When a solid composition in tablet form is prepared, the principal active ingredient is mixed with a pharmaceutical carrier such as gelatin, starch, lactose, magnesium stearate, talc, gum arabic or analogs. Tablets may be coated with sucrose or other suitable materials or may be treated in such a way that they have extended or delayed activity and that they continuously release a predetermined quantity of active principle.

A preparation in gelatin capsules is obtained by mixing the active compound with a diluent and by pouring the mixture obtained into soft or hard gelatin capsules.

A preparation in syrup or elixir form may contain the active ingredient together with a sweetener, an antiseptic, as well as a flavoring agent and a suitable colorant.

Water-dispersible powders or granules may contain the active ingredient in mixture with dispersion or wetting agents, or suspension agents, as well as with flavor correctors or sweeteners.

Midodrine, desglymidodrine, harmol, harmol dimers, brinzolamide and rilmenidine, derivatives thereof or mixtures thereof can be employed in therapy alone or in combination with at least one other active agent. These can be adjuvants for improving the activity of the compounds, or other active agents known for their use in the treatment of viral infections. Such active agents are well-known to those persons skilled in the art and are available commercially or are described in reference works such as *Le Dictionnaire Vidal*. These other active agents can in particular be selected from the active agents suitable to treat viral infections and more particularly to treat influenza virus infections.

Preferably, the antiviral or anti-influenza agent is selected from oseltamivir, zanamivir, peramivir, amantadine, rimantadine, ribavirin and arbidol.

The invention further relates to a product comprising a compound selected from midodrine, desglymidodrine, harmol, harmol dimers, brinzolamide and rilmenidine, as well as another antiviral agent as a combination product for simultaneous, separated or staggered use in therapy, and in particular in the prevention and treatment of viral infections.

The invention further relates to the use of at least one compound selected from midodrine, desglymidodrine, harmol, harmol dimers, brinzolamide, rilmenidine, and derivatives thereof for the manufacture of a drug to prevent or treat influenza.

The invention further relates to therapeutic methods to treat viral infections and more particularly influenza virus infections in man wherein an effective quantity of a compound selected from midodrine, desglymidodrine, harmol, harmol dimers, brinzolamide, rilmenidine and derivatives thereof is administered to a patient.

The invention further relates to therapeutic methods to treat viral infections and more particularly influenza virus infections in animals wherein an effective quantity of a compound selected from midodrine, desglymidodrine, harmol, harmol dimers, brinzolamide, rilmenidine and derivatives thereof is administered to an animal. Advantageously, the animal is a domesticated animal such as, for example, a pig, horse, chicken or turkey, dog, cat, etc.

BRIEF DESCRIPTION OF THE FIGURES

FIG. 2: Evaluation of the antiviral activity of the molecules on various viruses FIG. 4: Table summarizing the antiviral properties of the molecules

EXAMPLES

A. Infection of Human A549 Cells by Representative Human and Avian Influenza A Viruses A549 (lung carcinoma) cells are maintained in culture in Dulbecco's Modified Eagle Medium (DMEM, BioWhittaker) supplemented with 10% (v/v) fetal calf serum, 2 mM L-glutamine, 100 U/ml penicillin and 100 μg/ml streptomycin, in an incubator at 37° C., in an atmosphere saturated with moisture containing 5% $CO_2$. At confluence, the cells are detached from the support by treatment with trypsin-EDTA and are re-seeded in a culture flask containing 15 ml of fresh medium. Three days before the infection step, $0.75 \cdot 10^6$ cells are distributed in 25 $cm^2$ (T25) flasks in medium with 10% fetal calf serum in such a way as to obtain 70-80% confluence during the infection (the number of cells is estimated at $3 \cdot 10^6$ cells/T25). The cells are infected by the various influenza A viruses with an MOI of 0.1 in DMEM, 2 mM L-glutamine, 100 U/ml penicillin, 100 μg/ml streptomycin and 0.5 μg/ml trypsin (five flasks per virus).

The viruses used are strains of human (H1N1 A/New Caledonia/20/99, H3N2 A/Moscow/10/99) and avian influenza A viruses (H5N1 A/Turkey/582/2006, H5N2 A/Finch/England/2051/94, H7N1 A/Chicken/Italy/2076/99).

B. Cytotoxicity Test and Evaluation of the Antiviral Activity of the Molecules The potentially antiviral molecules were tested ex vivo on A549 cells. All the molecules were dissolved in water except rilmenidine which was taken up in DMSO and brinzolamide which was tested with its excipients in Azopt ophthalmic suspension.

These molecules are tested on A549 cells at 100% confluence in 96-well plates (prepared three days before with $0.15 \cdot 10^5$ cells/well in such a way as to obtain 100% confluence only on the day of the test). The cells are incubated for 6 h with various concentrations of molecules diluted in 150 μl of infection medium per well and then 50 μl per well of viral suspension is added (or 50 μl infection medium in the plate of uninfected cells). A cytotoxicity test and a virus quantification test are carried out after 65 h of incubation at 37° C. under 5% $CO_2$.

Figure 1:
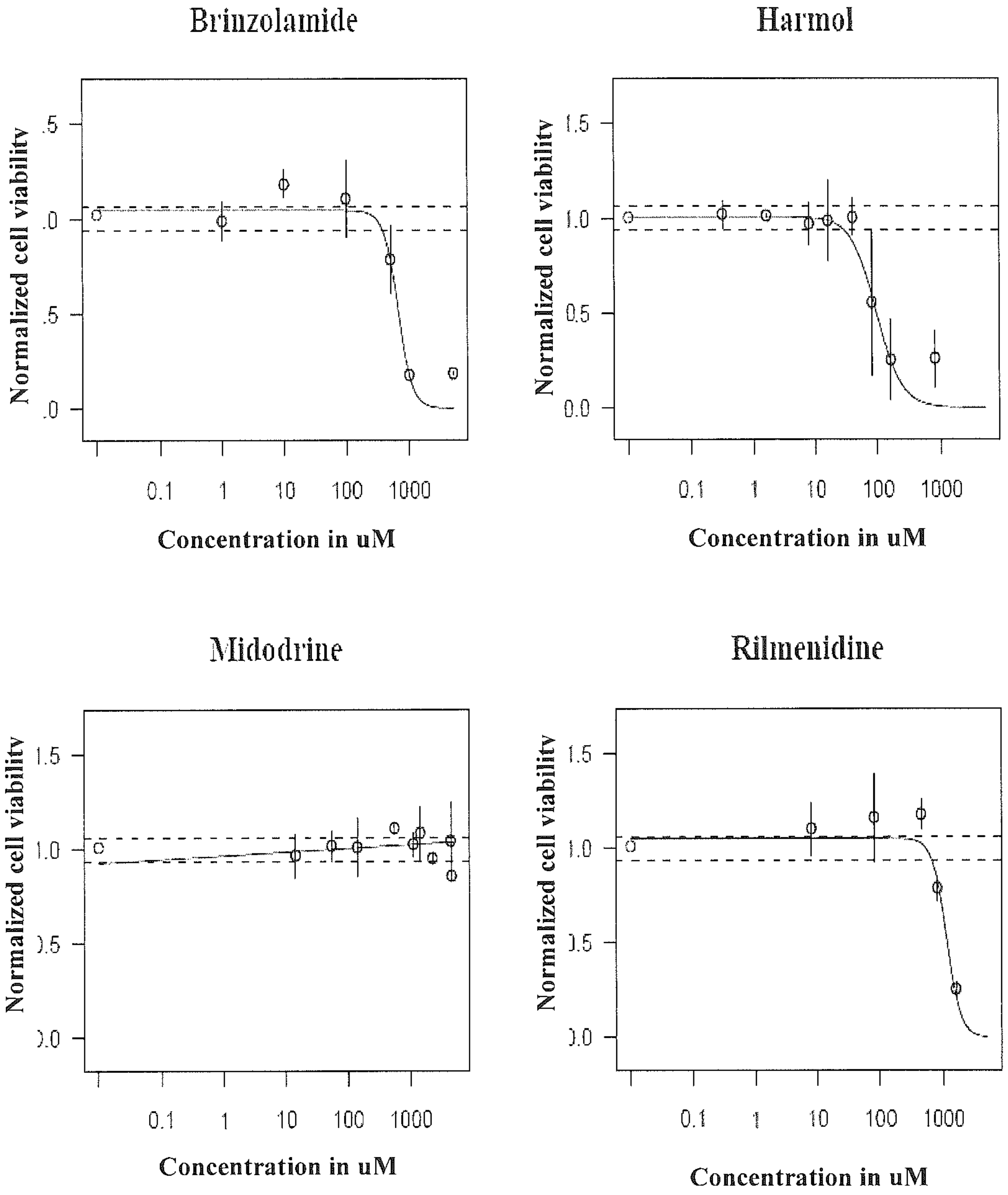
FIG. 1: Determination of the zones of cytotoxicity of the molecules

Cytotoxicity of the various molecules is determined in each test in a plate of uninfected cells by a Neutral Red test, which is a vital dye of lysozymes. After incubating the cells for 3 h in the presence of 1.55% Neutral Red and fixing for one minute with a formol/calcium mixture (40%/10%), the cells are lysed with 2% acetic acid and absorbance is read at 550 nm. The ratio of absorbance in each well to mean absorbance of the control cell wells (not treated with the molecules) is calculated and indicated on the diagrams as a cell viability index. The results are represented molecule by molecule in FIG. 1. These results are a compilation of five independent tests. They make it possible to define the concentrations of molecules resulting in 50% cytotoxicity ($CC_{50}$): brinzolamide starting from 665.5 mM, 95 mM harmol and 1125 mM rilmenidine.

The effect on viral production is tested on human (H1N1 A/New Caledonia/20/99, H3N2 A/Moscow/10/99) and avian influenza A virus strains (H5N1 A/Turkey/582/2006, H5N2 A/Finch/England/2051/94, H7N1 A/Chicken/Italy/2076/99) with two multiplicities of infection (MOI): MOI=0.2 and MOI=2. After 65 h of infection, the quantity of virus produced is estimated by a neuraminidase activity test. For this test, 25 μl of viral suspension is incubated for 1 h at 37° C. with 75 μl of MUN substrates (5 mM) diluted extemporaneously to 1/75 in MES (32.5 mM) $CaCl_2$ (4 mM) reaction buffer, pH 5.8. The reaction is quenched with 150 μl of glycine buffer (50 mM, pH 10.4) and then read on a fluorometer ($\lambda_{exc}$ 355 nm and $\lambda_{em}$ 460 nm). In the same manner as for cytotoxicity, the ratio of fluorescence intensity in each well to the intensity of mean fluorescence of the control cell wells (not treated with the molecules) is calculated and indicated on the diagrams as a viral production index.

In each test, each concentration of molecules is tested in two wells (duplicate). The concentration range was selected according to the cytotoxicity results represented in FIG. 1. The results, from two independent tests, are represented molecule by molecule for each virus in FIG. 2.

C. Evaluation of the Molecules on Infection Efficiency (Viral Entry)

According to our hypothesis, antiviral molecules have an effect on cell metabolism by inducing a cellular context that is not favorable to infection. To prove that the drugs tested act specifically on cell state and not on the virus and its capacity to infect cells (alteration of the viral membrane, inhibition of viral surface glycoproteins HA and NA, competitive agonist on the cell receptors of influenza viruses, etc.), two parallel tests were carried out on the H3N2 virus.

The first test consists of incubating undiluted virus for 15 h at 37° C. with various concentrations of the molecules c as described above. A dilution to 1/3 in fresh infection medium is then prepared and 50 μl of this dilution is used per well of MW96 to infect confluent A549 cells previously washed and in 150 μl of fresh infection medium. After 15 minutes of infection, the medium is removed, the cells are rinsed twice and 200 μl of medium is added per well. During these 15 minutes of infection, the drugs are at a final concentration of c/48, it is estimated that this concentration is too low and the contact time with the cells is too short to induce a cellular effect. The virus is diluted to 1/16 final, which leads, for the drug-free controls, to a signal that is quantifiable and not saturating at the end of the test. After 5 hours (which represents an infection cycle), the number of infected cells is estimated by quantifying cellular neuraminidase. If the number of infected cells is less than the drug-free control, this indicates that the virus has been disrupted or destroyed during the 12 h of incubation with the molecule.

The second test consists of incubating the cells with drugs for 15 h at 37° C. carried out in the same manner as the first 6 hours of incubation described above. After 24 h, the cells are washed twice in medium and incubated with 150 μl of fresh infection medium per well. Infection is carried out for 15 minutes by adding 50 μl/well of virus diluted to 1/16 (thus to 1/64 final) and then the cells are rinsed twice and 200 μl of medium is added per well. After 5 h, the number of infected cells is estimated by quantifying cellular neuraminidase. In this test, the viruses are never in contact with the drugs. If the cells treated beforehand with the molecules are less infected than the controls, this shows that the molecules had an action on the cell to induce an antiviral environment.

To quantify cellular neuraminidase in these two tests at the end of 5 h of infection, the cells are washed in PBS and then lysed with 25 μl/well of 1× Triton in PBS for 1 h at room temperature with agitation. This 25 μl of lysate is incubated for 1 h at 37° C. with 75 μl of MUN substrates (5 mM) diluted extemporaneously to 1/75 in MES $CaCl_2$ reaction buffer. The reaction is quenched with 150 μl of 50 mM glycine buffer and is read on a fluorometer ($\lambda_{exc}$ 355 nm and $\lambda_{em}$ 460 nm).

Figure 3:
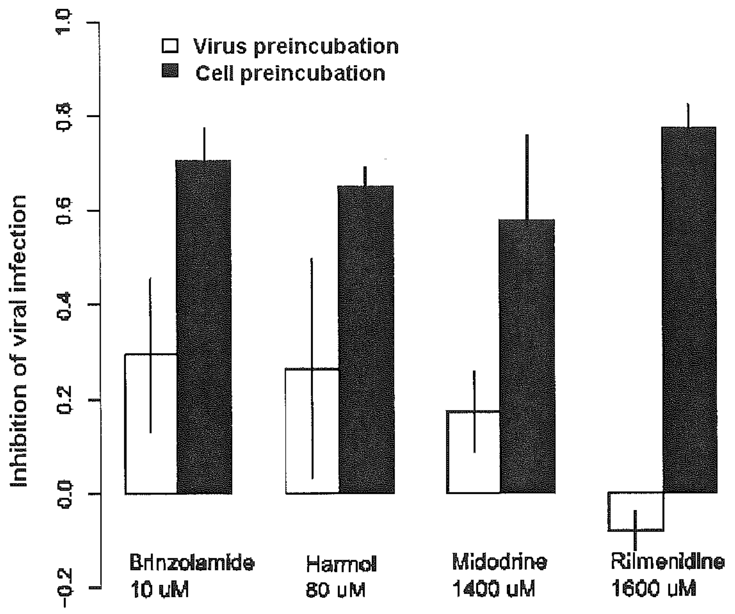
FIG. 3: Evaluation of the activity of the molecules on the viruses and their cell entry

The results of these two tests are presented in FIG. 3 and show that the effect of the molecules described in B (FIGS. 1 and 2) is always predominant on the cells, compared with the direct effect on the viruses.

D. Evaluation of the Molecules on Pandemic H1N1 Virus Production

The molecules were evaluated for their antiviral activity on pandemic H1N1 virus by following the same procedures and experimental conditions described above (A and B).

For these tests, the virus was tested with an MOI of 2 in two independent procedures. The results are represented in FIG. 2.

The results obtained with pandemic H1N1 virus are completely consistent with those obtained with the viruses chosen beforehand for the study. The molecules harmol and midodrine are also characterized by antiviral activity. In terms of the molecules brinzolamide and rilmenidine, which demonstrated antiviral activity only for certain viruses, they do not seem to have an impact on pandemic H1N1 virus under the conditions tested.

E. Summary of the Properties of Each Molecule on the Viruses

The selectivity index of the molecules is the ratio between $CC_{50}$ and $EC_{50}$. It is an accepted fact that a weak inhibitor has an SI between 2 and 10, a moderate inhibitor has an SI between 10 and 50 and a strong inhibitor has an SI greater than 50.

According to our results (see FIG. 4), midodrine is a moderate inhibitor and the other molecules are weak-to-moderate inhibitors.

Midodrine inhibits the infectious cycle of all the viruses tested except H7N1 virus. Harmol inhibits the infectious cycle of H3N2, H5N2 and H5N1 viruses and of low-MOI pandemic H1N1 virus.

Brinzolamide inhibits primarily the infectious cycle of H3N2 virus and low-MOI H1N1 and H7N1 viruses.

Rilmenidine inhibits the infectious cycle of H3N2, H1N1 and H5N2 viruses.

REFERENCES

WO 2009/047298
WO 2007/044752
WO 2009/065116

The invention claimed is:

1. A pharmaceutical or veterinary composition comprising midodrine and oseltamivir.

2. The pharmaceutical or veterinary composition according to claim 1, further comprising a suitable pharmaceutical carrier.

3. A product comprising at least midodrine and oseltamivir as a combination suitable for simultaneous, separated or staggered administration.

4. A method to treat influenza virus infections wherein a composition comprising midodrine and oseltamivir is administered to a patient in need thereof.

* * * * *